United States Patent [19]

Chen et al.

[11] Patent Number: 4,933,283
[45] Date of Patent: Jun. 12, 1990

[54] PROCESS FOR CONVERTING CELLULOSIC MATERIALS TO HYDROCARBON PRODUCTS

[75] Inventors: Nai Y. Chen, Titusville; Leonard R. Koenig, Trenton, both of N.J.

[73] Assignee: Mobil Oil Corporation, New York, N.Y.

[21] Appl. No.: 120,681

[22] Filed: Nov. 12, 1987

Related U.S. Application Data

[63] Continuation of Ser. No. 734,209, May 15, 1985, abandoned, which is a continuation-in-part of Ser. No. 430,458, Sep. 30, 1982, abandoned.

[51] Int. Cl.$^5$ .................. C12P 5/00; C12P 7/08; C12P 7/10; C07C 1/00
[52] U.S. Cl. .................. 435/166; 435/163; 435/165; 435/252; 585/240; 585/242
[58] Field of Search ............ 435/161, 162, 163, 166, 435/167, 252; 585/240, 242

[56] References Cited

U.S. PATENT DOCUMENTS

| | | | |
|---|---|---|---|
| 2,551,579 | 5/1951 | Berl | 585/240 |
| 3,212,933 | 10/1965 | Hess et al. | 127/37 |
| 3,936,353 | 2/1976 | Chen | 435/163 |
| 3,998,898 | 12/1976 | Chang et al. | 585/408 |
| 4,086,262 | 4/1978 | Chang et al. | 518/716 |
| 4,199,371 | 4/1980 | Regnault et al. | 127/37 |
| 4,266,981 | 5/1981 | Tsao et al. | 127/37 |
| 4,300,009 | 11/1981 | Haag et al. | 585/638 |
| 4,308,411 | 12/1981 | Frankiewicz | 585/240 |
| 4,515,892 | 5/1985 | Chen et al. | 435/161 |
| 4,549,031 | 10/1985 | Chen et al. | 585/408 |

OTHER PUBLICATIONS

Glushenko et al., (1981), Chemical Abstracts, vol. 95, No. , p. 95, item #95469h.

*Primary Examiner*—David M. Naff
*Attorney, Agent, or Firm*—Alexander J. McKillop; Charles J. Speciale; Marina V. Schneller

[57] ABSTRACT

Cellulosic materials are converted to hydrocarbons by hydrolyzing cellulosic materials to produce a mixture of fermentable sugars and unfermentable furfural, fermenting the mixture to obtain a fermented mixture containing fermented product and unfermented furfural and contacting the fermented mixture with a highly siliceous crystalline zeolite catalyst under conditions of temperature and pressure to convert the fermented mixture to a hydrocarbon-containing product. Preferably, an oxygenated organic compound such as methanol, ethanol or dimethylether is mixed with the fermented mixture prior to contact with the catalyst.

14 Claims, No Drawings

PROCESS FOR CONVERTING CELLULOSIC MATERIALS TO HYDROCARBON PRODUCTS

This application is a continuation of application Ser. No. 734,209, filed May 15, 1985, now abandoned, which is a continuation-in-part of application Ser. No. 430,458, filed Sept. 30, 1982, now abandoned, the entire contents of which are incorporated herein by reference.

This invention relates to a process for converting cellulosic materials to hydrocarbon products. More particularly, it refers to a method for producing hydrocarbons by hydrolyzing cellulosic materials to form a mixture of fermentable sugars and unfermentable by-products. The unfermentable by-products, such as furfural and furfural derivatives, are converted to hydrocarbon products by contacting them with a catalyst comprising highly siliceous crystalline zeolite materials, at hydrocarbon conversion conditions.

The conversion of solid biomass materials, such as cellulose, into hydrocarbon products is well known. For example, U.S. Pat. No. 4,308,411 to Frankowicz discloses a method of converting organic waste to hydrocarbons, which method comprises pyrolyzing organic waste to form a mixture containing oxygenated hydrocarbons. The oxygenated hydrocarbons are contacted with a crystalline zeolite material at conditions which convert the oxygenated hydrocarbons into liquid hydrocarbons such as gasoline U.S. Pat. No. 3,998,898 to Chang et al., incorporated herein by reference, discloses an improved method for converting oxygenated hydrocarbon compounds by mixing said compounds with oxygenated compounds which are easily converted to hydrocarbons, prior to conversion over zeolitic materials. Examples of such easily convertible oxygenated organic compounds include aliphatic alcohols, ethers, acetals, and/or analogs thereof.

It is known in the art to hydrolyze cellulosic materials with an acid to form pentose and hexose sugars as well as unfermentable by-products. Various methods for hydrolyzing cellulose are disclosed in U.S. Pat. No. 3,212,933 to Hess et al., U.S. Pat. No. 4,199,371 to Reneault et al., and U.S. Pat. No. 4,266,981 to Tsao et al., all of which are incorporated herein by reference It has also been found that the sugars produced from hydrolysis can be converted to hydrocarbon compounds by mixing said sugars with an easily convertible aliphatic organic oxygenated compound, such as ethanol U.S. Pat. No. 4,549,031 incorporated herein by reference, discloses such a method.

While the above methods exemplify ways in which cellulosic materials can be converted into useful hydrocarbon products, room for improvement still exists. Typically, hydrolysis of cellulosic materials generates between 7 and 50% waste by-products consisting mainly of furfural and furfural derivatives. Unlike sugars, these by-products are not fermentable. In order to increase the hydrocarbon yield from a given amount of cellulosic material it would be desirable to find a way of converting these unfermentable hydrolysis by-products to hydrocarbons.

The present invention is directed to a process for converting cellulosic materials to hydrocarbons which comprises hydrolyzing cellulosic materials to form a mixture containing water, fermentable sugars and unfermentable by-products such as furfural and furfural derivatives. The mixture is then exposed to fermentation conditions to effect fermentation of the fermentable component therein. The resulting product mixture contains both fermentation products and unfermentable by-products of hydrolysis as well as water. Some or all of the water may be removed by any suitable method such as selective sorption, fractional distillation or flashing. U.S. Pat. No. 3,936,353, incorporated herein by reference, teaches hydrocarbon conversion of fermentation products which contain substantial amounts of water.

After water removal, the fermentation product mixture is contacted under suitable hydrocarbon conversion conditions with a catalyst comprising a highly siliceous crystalline zeolite having a silica to alumina ratio of at least about 12 and a Constraint Index of about 1 to 12, to form a hydrocarbon-containing product. Preferably, the product mixture after fermentation is contacted with the catalyst in a moving bed reactor or a fluidized bed reactor. In one embodiment of the present invention, the easily convertible organic compounds such as methanol, ethanol and/or dimethyl ether are added to the product mixture prior to contacting with the catalyst comprising a highly siliceous crystalline zeolite, under hydrocarbon conversion conditions. In one embodiment of the invention, water may be separated from the mixture obtained by fermentation by contacting the mixture with highly siliceous zeolite according to the method disclosed in U.S. Pat. No. 4,515,892 to Chen et al, incorporated herein by reference.

The cellulosic materials which may be employed in the process of the present invention broadly comprise those classes of materials which stem from plant growth processes. Such materials are often readily available as waste by-products of various industries. For example, they may comprise such plant-derived materials as oat hulls, corn stalks, and bagasse. In particular, however, they comprise the woods of various species of trees. The wood may be used in the instant process in the form of sawdust, wood shavings, thin chips, flakes, and the like. To be susceptible to efficient utilization, however, cellulosic materials are preferably broken down into particles of about 200 mesh or smaller. By thus increasing surface area, hydrolysis of these materials is enhanced and accelerated.

The hydrolysis step of the present invention whereby cellulosic materials are converted into fermentable sugars such as glucose and five-carbon sugars and unfermentable by-products may be accomplished through any suitable method known in the art. In one embodiment of the present invention, disclosed in U.S. Pat. No. 4,266,981 to Tsao et al., a dilute solution of sulfuric acid containing from about 5 to 50 g of $H_2SO_4$ in a kilogram of aqueous solution is combined with lcellulosic materials such as wood chips. The resulting mixture is heated to a temperature ranging between about 100° C. to 350° C. The cellulosic material is thus hydrolyzed to produce glucose from cellulose and five-carbon sugars from hemi-cellulose. Where the reaction temperature exceeds the boiling point of the dilute acid, the hydrolysis reaction is carried out in a pressurized reactor. At high temperatures, glucose and five-carbon sugars are catalyzed by the acid to form furfural and its derivatives which can react further to form other undesirable by-products. Such a dilute acid process will typically yield about 50 wt. % glucose and 50 wt. % unfermentable by-products.

Among the acid hydrolysis processes suited for use in the present invention are: those employing concentrated sulfuric acid such as that method disclosed by Bose et al. (see Bharati Bose, T. R. Ingle. and J. C. Bose, "Saccharification of Groundnut Shell Pulp with Sulfuric Acid", Indian Journal of Technology, Vol. II, September 1973, pp. 391-393); those employing a dilute sulfuric acid hydrolysis stage followed by a concentrated sulfuric acid hydrolysis stage, (see U.S. Pat. No. 4,266,981 to Tsao et al.), and those employing concentrated hydrochloric acid (see U.S. Pat. No. 3,251,716 to Porter and U.S. Pat. No. 4,199,371); all of which are incorporated herein by reference.

In addition, enzyme-catalyzed hydrolysis may be used as a substitute or supplement to acid hydrolysis in the present invention (see Ernest and Katzen, Chem-Tech, October, 1980, p. 610; U.S. Pat. No. 4,237,226 to Grethlein, incorporated herein by reference).

In a simple embodiment of the present invention, the product of cellulose hydrolysis containing unfermentable cellulose hydrolysis by-products and fermentables such as sugars are exposed to suitable fermentation conditions, examples of which are set out in U.S. Pat. No. 3,936,353. The resulting mixture which includes oxygenated hydrocarbon by-products such as furfural and furfural derivatives is passed through a fluidized bed reactor containing a highly siliceous crystalline zeolite catalyst, such as HZSM-5, which reactor is maintained at a temperature ranging from about 300° to 800° C., preferably from about 400 to 650° C., e.g., about 550° C., and pressures ranging from about 1 to 100 Atm, preferably from about 1 to 20 Atm, say, about 1 Atm. The reactor feed is adjusted to a weight hourly space velocity ranging from about 1 to 100, preferably ranging from about 0.9 to 5.0, e.g., about 1. The foregoing reactor conditions are also suited to the alternative embodiments hereinafter described.

When a furfural-containing feed is passed through a fluidized bed reactor under the aforementioned conditions, about 38% of the available carbon is converted to hydrocarbon liquid. In addition, about 24 to 30% of the available carbon in the oxygenate is converted to carbon monoxide which may be separated from the hydrocarbon-containing product and employed as synthesis gas in various hydrocarbon-producing processes such as Fischer-Tropsch, wherein it is contacted with a Fischer-Tropsch catalyst under suitable conditions. See, e.g., U.S. Pat. No. 4,086,262 to Chang et al., incorporated herein by reference, which discloses a method for producing hydrocarbons from synthesis gas by employing a Fischer-Tropsch catalyst and an acidic crystalline aluminosilicate. As a result of incorporating such subsidiary synthesis gas processes into the method of the present invention, substantial increases in the production of desired products such as liquid hydrocarbons can be achieved.

Alternatively, the hydrolysis mixture containing ferentable sugars and unfermentable by-products can be mixed before or after fermentation with easily convertible oxygenated hydrocarbons such as methanol, dimethyl ether and/or ethanol The resulting mixture is contacted with a catalyst under hydrocarbon conversion conditions, in accordance with the method disclosed in U.S. Pat. No. 3,998,898 to Chang et al. or U.S. Pat. No. 4,549,031. Preferably, the proportion of ferentable sugars to unfermentable by-products and easily convertible oxygenated compounds can be such that the resulting mixture has an effective hydrogen index (EHI) of about 1. The EHI is defined in terms of atomic ratios as follows:

$$EHI = \frac{(H) - 2(O) - 3(N) - 2(S)}{(C)}$$

where H, C, O, N, S are the number of atoms per formula weight of sample of hydrogen, carbon, oxygen, nitrogen and sulfur, respectively, as determined by elemental analysis. A suitable mixture of fermentable sugars, unfermentable by-products and easily convertible oxygenated hydrocarbons may contain from 2 parts by weight glucose to 2 parts by weight furfural to 4 parts by weight ethanol.

Because unfermentable by-products of cellulose hydrolysis such as furfural have relatively low hydrogen to carbon ratios, it is generally necessary to prevent poisoning of the resulting catalyst caused by coke deposition and build-up. In one embodiment of the present invention, coke build-up is mitigated by employing a moving bed or fluidized bed reactor. Such an arrangement permits regeneration of the catalyst by raising the reactor to combustion temperatures and burning off any accumulated coke in an oxidizing atmosphere. The catalyst is preferably regenerated at about 1 to 30 minute intervals, preferably about 10 minute intervals.

The catalyst employed in the hydrocarbon conversion of the present invention comprises a particular type of crystalline aluminosilicate zeolite material which exhibits unusual properties. Although such zeolites have unusually low alumina contents, i.e., high silica to alumina mole ratios, they are very active even when the silica to alumina mole ratio exceeds 30. Such activity is surprising, since catalytic activity is generally attributed to framework aluminum atoms and/or cations associated with these aluminum atoms. These zeolites retain their crystallinity for long periods in spite of the presence of steam at high temperatures which induces irreversible collapse of the framework of other zeolites, e.g., of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolties is that it provides a selective constrained access to and egress from the intracrystalline free space by virtue of having an effective pore size intermediate between the small pore Linde A and the large pore Linde X, i.e., the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g., 70 or above or even 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description.

Members of this particular class of zeolites, after activation, acquire an intracrystalline sorption capacity for normal hexane which is greater than that for water, i.e., they exhibit "hydrophobic" properties. This hydrophobic character can be used to advantage in some applications.

The zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraint Index (CI) values for some typical materials are:

| Zeolite | Constraint Index |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA-Offretite | 3.7 |
| Clinoptilolite | 3.4 |
| Beta | 0.6 |
| H-Zeolon (mordenite) | 0.4 |
| REY | 0.4 |
| Amorphour Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g., 0.9, or somewhat greater than 12, e.g., 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The particular class of zeolites defined herein is exemplified by ZSM-5, ZSM-5/ZSM-11 intermediates, ZSM-11, ZSM-12, ZSM-23, ZSM-35, ZSM-38, ZSM-48 and other similar materials.

ZSM-5 is described in greater detail in U.S. Pats. No. 3,702,886 and Re 29,948. The entire descriptions contained within those patents, particularly the X-ray diffraction pattern of therein disclosed ZSM-5, are incorporated herein by reference.

ZSM-5/ZSM-11 intermediate compositions are described in U.S. Pat. No. 4,229,424. That description, and in particular the X-ray diffraction pattern of said compositions disclosed therein, is incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire contents thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in U.S. Pat. No. 4,375,573, the entire content of which is incorporated herein by reference.

It is to be understood that by incorporating by reference the foregoing patent documents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-5/ZSM-11 intermediates, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired.

Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article, Zeolite Structure, by W. M. Meier. This paper, the entire contents of which are incorporated herein by reference, is included in Proceedings of the Conference on Molecular Sieves (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, ZSM-11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 50 percent by weight of the original alkali metal contained in the zeolite as-synthesized, usually 0.5 percent by weight or less, may be used as precursors to the alkaline-earth metal modified zeolites of the present invention. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing conversion processes of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring in or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The following examples will serve to illustrate the process of this invention without limiting the same.

EXAMPLE 1

Hydrolysis of Cellulosic Materials And Fermentation of Hydrolysis Product 100 grams of wood particles of about 200 mesh are combined with 300 ml. of a dilute sulfuric acid solution containing 50 grams of $H_{SO4}$ in a kilogram of aqueous solution. The resulting mixture is placed in a pressurized reactor which is raised to a temperature of about 350° C. This temperature is maintained until hydrolysis of the wood particles is complete. The resulting products of hydrolysis comprise a yield of about 50% glucose and 50% furfural and furfural derivatives based on the available cellulose in the starting material. The glucose-furfural mixture is then passed to a fermenter containing a yeast, *Saccharomyces cerevisiae*, which is maintained at fermentation conditions including atmospheric pressure and a temperature of about 37° C. The product mixture resulting from fermentation is thereafter contacted with a hydrophobic HZSM-5 having a silica to alumina mole ratio of about 200. An organic containing product which comprises furfural and alcohol is thereafter desorbed from the zeolite.

EXAMPLE 2

Conversion of Furfural-Methanol Mixture over HZSM-5 to Form Hydrocarbons

A mixture containing 18.2 g. of furfural, 74.2 g. of methanol and 7.6 g. of water was passed through a fluidized bed of HZSM-5, which had been steamed to an alpha value of about 40, at 550° C. and at a WHSV of 2.0. The results of analysis of the product are set out in Table I. The total conversion of reactant carbon to hydrocarbon was 40.21% by weight, 32.46% by weight of which was attributable to methanol, while the remainder was attributable to furfural. Small amounts of CO (5.80%) were obtained. The conversion efficiency of furfural to hydrocarbon was significantly increased by the presence of methanol in the furfural feed. While pure furfural feed is converted with an efficiency of 28.11% at a WHSV of about 2, the presence of alcohol in the feed increased the conversion efficiency of furfural to 42.57%.

TABLE I

| Furfural and Methanol over HZSM-5 at 550° C. | |
|---|---|
| | Weight Percent |
| Feed Components | |
| Furfural | 18.2% |
| Water | 7.6% |
| Methanol | 74.2% |
| Product Components | |
| Methane | 0.51% |
| Ethane | — |
| Ethene | 3.78% |
| Propane | 0.30% |
| Propene | 6.73% |
| Isobutane | 1.34% |
| n-Butane | 0.04% |
| Butenes | 1.54% |
| Furan | 0.75% |
| Hydrocarbon Liquid | 25.93% |
| CO | 5.80% |
| $CO_2$ | 1.16% |
| Water | 51.01% |
| Coke | 1.07% |
| Total Conversion to Hydrocarbon | 40.21% |
| Hydrocarbon Production Attributed to Methanol | 32.46% |
| Hydrocarbon Production Attributed to Furfural | 7.75% |

Conversion Efficiency of Furfural to Hydrocarbon =
$$\frac{\text{Weight Percent of HC Produced from Furfural}}{\text{Weight Percent of Furfural in Feed}} \times 100\% = 42.57\%$$

It is claimed:

1. A process for converting cellulosic materials to hydrocarbons which comprises (a), (b), (c), and (d) wherein (a) comprises hydrolyzing said cellulosic materials to form a mixture which comprises fermentable sugars and unfermentable furfural; wherein (b) comprises exposing said mixture to fermentation conditions to effect fermentation of said fermentable sugars and to produce a mixture containing a fermentation product admixed with said unfermentable furfural; wherein (c) comprises combining said fermentation product admixed with unfermentable furfural with methanol prior to (d); and wherein (d) comprises thereafter contacting the resulting mixture which contains fermentation product, unfermentable furfural and methanol and a highly siliceous crystalline zeolite catalyst having a silica to alumina mole ratio of at least 70 and a Constraint Index of 1 to 12 under conditions of temperature and pressure sufficient to convert said mixture to a hydrocarbon-containing product.

2. A process of claim 1 wherein said contacting with said catalyst occurs in a fluidized bed reactor.

3. A process of claim 1 wherein said contacting with said catalyst occurs in a moving bed reactor.

4. A process of claim 1 wherein said highly siliceous crystalline zeolite is selected from the group consisting of ZSM-5, ZSM-11, ZSM-12, ZSM-23, ZSM-35, ZSM-38 and ZSM-48.

5. A process of claim 1 wherein said contacting with said catalyst is carried out at temperatures ranging from about 300° to 800° C., pressures ranging from about 1 to 100 Atm., and a weight hourly space velocity ranging from about 0.1 to 100.

6. A process of claim 1 wherein said catalyst is periodically oxidatively regenerated.

7. A process of claim 1 wherein said catalyst is periodically oxidatively regenerated every 1 to 30 minutes.

8. A process of claim 1 wherein said catalyst is periodically oxidatively regenerated every 10 minutes 9. A process of claim 1 wherein water is removed from the mixture resulting from fermentation prior to contacting said mixture with said catalyst.

10. A process of claim 1 wherein said hydrocarbon-containing product contains carbon monoxide.

11. A process of claim 1 wherein said highly siliceous crystalline zeolite is ZSM-5.

12. A process of claim 1 wherein said contacting with said catalyst is carried out at temperatures ranging from about 400° to 650° C., pressures ranging from about 1 to 20 Atm., and weight hourly space velocity ranging from about 0.9 to 5.

13. A process of claim 1 wherein said contacting with said catalyst is carried out a temperature of about 550° C., pressure of about 1 Atm., and a weight hourly space velocity of about 1.

14. A process of claim 11, wherein said contacting with said catalyst is carried out a temperatures ranging from about 400° to 650° C., pressures ranging from about 1 to 20 Atm., and weight hourly space velocity ranging from about 0.9 to 5.

* * * * *